United States Patent
Shimmura et al.

(10) Patent No.: US 11,332,773 B2
(45) Date of Patent: May 17, 2022

(54) RAPID TUMORIGENICITY SCREENING SYSTEM

(71) Applicant: KEIO UNIVERSITY, Tokyo (JP)

(72) Inventors: Shigeto Shimmura, Tokyo (JP); Shin Hatou, Tokyo (JP); Emi Inagaki, Tokyo (JP); Kazuo Tsubota, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 178 days.

(21) Appl. No.: 16/635,094

(22) PCT Filed: Jul. 31, 2018

(86) PCT No.: PCT/JP2018/028654
§ 371 (c)(1),
(2) Date: Jan. 29, 2020

(87) PCT Pub. No.: WO2019/026903
PCT Pub. Date: Feb. 7, 2019

(65) Prior Publication Data
US 2020/0308621 A1    Oct. 1, 2020

(30) Foreign Application Priority Data

Jul. 31, 2017 (JP) .............................. JP2017-148605

(51) Int. Cl.
*C12Q 1/02* (2006.01)
*A01K 67/027* (2006.01)
*G01N 33/15* (2006.01)

(52) U.S. Cl.
CPC .......... *C12Q 1/025* (2013.01); *A01K 67/0271* (2013.01); *G01N 33/15* (2013.01); *A01K 2227/105* (2013.01); *A01K 2267/0331* (2013.01)

(58) Field of Classification Search
CPC ............ A61K 2039/5152; A61B 5/413; A61B 17/0231; C12Q 1/025; A01K 2207/12
USPC .................................................. 424/9.1, 9.2
See application file for complete search history.

(56) References Cited

PUBLICATIONS

White et al., Cancer Research, vol. 50, pp. 3078-3086, May 1990.*
Wang et al., The Journal of Immunology, vol. 171, pp. 2789-2796, 2003.*
Roubeix et al., Intraocular pressure reduction and neuroprotection conferred by bone marrow-derived mesenchymal stem cells in an animal model of Glaucoma, 2015, Stem Cell Research & Therapy, 6:177, pp. 1-13 (Year: 2015).*
Boone et al., "Quantitative Tumorigenicity Assays Using the Anterior Chamber of the Mouse Eye," Cancer Res., 28(9): 1734-1737 (1968).
Kawamata et al., "Design of a Tumorigenicity Test for Induced Pluripotent Stem Cell (iPSC)-Derived Cell Products," J. Clin. Med., 4(1): 159-171 (2015).
Mathiesen et al., "Prolonged survival and vascularization of xenografted human glioblastoma cells in the central nervous system of Cyclosporine A treated rats," Cancer Lett., 44(2): 151-156 (1989).
Wang et al., "Role of TRAIL and IFN-γ in CD4+T Cell-Dependent Tumor Rejection in the Anterior Chamber of the Eye," J. Immunol., 171(6): 2789-2796 (2003).
White et al., "Heterotransplantation of Human Lymphoid Neoplasms Using a Nude Mouse Intraocular Xenograft Model," Cancer Res., 50(10): 3078-3086 (1990).
Zhu et al., "Transplantation of iPSC-derived TM cells rescues glaucoma phenotypes in vivo," Proc. Natl. Acad. Sci. U.S.A., 113(25): E3492-E3500 (2016).
Hato et al., "Method for injecting and transplanting iPS cell-derived cornea endothelial substitute cells into anterior chamber," Regenerative Medicine, 14: 236, Abstract No. O-34-6 (Feb. 1, 2015).
Higuchi et al., "A Novel Enhanced Green Fluorescent Protein-Expressing NOG Mouse for Analyzing the Microenvironment of Xenograft Tissues," Exp. Anim., 63(1): 55-62 (2014).
Kanemura et al., "Tumorigenicity Studies of Induced Pluripotent Stem Cell (iPSC)-Derived Retinal Pigment Epithelium (RPE) for the Treatment of Age-Related Macular Degeneration," PLoS One, 9(1): e85336 (2014).
Masuda et al., "A Simplified In Vitro Teratoma Assay for Pluripotent Stem Cells Injected Into Rodent Fetal Organs," Cell Med., 3(1-3): 103-112 (2012).
Mizukami et al., "MHC-Matched Induced Pluripotent Stem Cells Can Attenuate Cellular and Humoral Immune Responses but Are Still Susceptible to Innate Immunity in Pigs," PLoS One, 9(6): e98319 (2014).
Ogawa et al., "Review about non-clinical tumorigenicity examination using human mesenchymal stem cell and HeLa cell," Regenerative Medicine, 16: 431, Abstract No. P-03-034 (Feb. 1, 2017).
Wang et al., "Reprogramming of mouse renal tubular epithelial cells to induced pluripotent stem cells," Cytotherapy, 15(5): 578-585 (2013).
Wang et al., "Reduced Immunogenicity of Induced Pluripotent Stem Cells Derived from Sertoli Cells," PLoS One, 9(8): e106110 (2014).

(Continued)

*Primary Examiner* — Misook Yu
*Assistant Examiner* — Dennis J Sullivan
(74) *Attorney, Agent, or Firm* — Leydig, Voit & Mayer, Ltd.

(57) ABSTRACT

The present invention provides a method for evaluating tumorigenicity of a test cell, including transplanting the cell into anterior chamber of an eye of an experimental animal, and observing the presence or absence of tumor formation. According to the present invention, tumorigenicity can be evaluated in a short period and conveniently.

12 Claims, 3 Drawing Sheets

(56) References Cited

PUBLICATIONS

Who Expert Committee on Biological Standardization, "Requirements for the use of animal cells as in vitro substrates for the production of biologicals," *WHO Technical Report Series*, 878: 19-56 (1998).
Japanese Patent Office, International Search Report in International Patent Application No. PCT/JP2018/028654 (dated Nov. 6, 2018).
Japanese Patent Office, Written Opinion of the International Searching Authority in International Patent Application No. PCT/JP2018/028654 (dated Nov. 6, 2018).

* cited by examiner tumor formation in anterior chamber of eye is observable over time due to good visibility tumor formation confirmed within one month transplantation — 2 weeks — 4 weeks immunodeficient rat

| time necessary for confirmation of tumor formation | |
|---|---|
| subcutaneous | anterior chamber of eye |
| several months or more | 3-4 weeks | verified with FFI-01 undifferentiated iPS cell line

RAPID TUMORIGENICITY SCREENING SYSTEM

CROSS-REFERENCE TO RELATED APPLICATIONS

This patent application is the U.S. national phase of International Patent Application No. PCT/JP2018/028654, filed Jul. 31, 2018, which claims the benefit of Japanese Patent Application No. 2017-148605, filed on Jul. 31, 2017, which are incorporated by reference in their entireties herein.

TECHNICAL FIELD

The present invention relates to a novel tumorigenicity screening system capable of evaluating tumorigenicity of a cell in a short period. The present invention also relates to a method for evaluating efficacy of an anticancer drug using the aforementioned screening system and the like.

BACKGROUND ART

In regenerative medicine using stem cells such as iPS cell, mesenchymal stem cell, neural stem cell and the like, ensuring the safety of the cells to be transplanted (especially reducing the risk of tumorigenesis) is one of the most important problems. When transplantation therapy using stem cells and differentiated cells induced therefrom is performed, it is necessary to certainly check the tumorigenicity of the cell. Based on cells used as the starting material, the risk of malignant transformation is higher in the order of ES/iPS cells, somatic stem cells, and somatic cells. In addition, ES/iPS cell-derived products need to be evaluated for the risk of teratoma formation due to residual pluripotent stem cells.

In addition, tumorigenicity is one of the endpoints also in the evaluation of the malignancy of various cancer cells, and judgment of the effect of an anticancer agent and the like.

As a tumorigenicity test, a method for evaluating tumor-forming ability by using immunodeficient animals such as mouse and the like and subcutaneously transplanting test cells into the animal body is widely practiced. However, this method requires a large number of animals and long-term observation for several months because the tumor cannot be detected until the tumor size becomes very large. According to the international guidelines for in vivo tumorigenicity test (non-patent document 1), it is necessary to subcutaneously administer $10^7$ cells to 10 animals such as nude mice and the like and examine by comparison with HeLa cells and the like for 16 weeks.

When tumor formation is observed in the first tumorigenicity test, or when the protocol such as induction method, manufacturing method or the like is modified after the tumorigenicity test, the tumorigenicity test must be repeated from the beginning. Therefore, the development of a novel in vivo screening system that can evaluate tumorigenicity in a shorter period of time and has small variation among individuals is desired. In vitro and in vivo assay systems for evaluating tumorigenicity including teratoma formation of cancer cells, pluripotent stem cells and differentiated cells induced therefrom conveniently and in a short period have been reported (non-patent documents 2-7). The former eventually requires an in vivo test to evaluate tumorigenicity in the microenvironment where the transplanted cells are engrafted. In the latter, since the cells are transplanted subcutaneously and the like, the evaluation of tumorigenicity becomes complicated.

Therefore, a screening system capable of evaluating tumorigenicity conveniently in a short period is still required.

DOCUMENT LIST

Non-Patent Documents non-patent document 1: "Requirements for Use of Animal Cells as in vitro Substrates for the Production of Biologicals" in WHO Expert Committee on Biological Standardization, 47th Report (1998) (technical report series number 878, TRS 878)
non-patent document 2: Cell Med., 3: 103-112 (2012)
non-patent document 3: Exp. Anim., 63(1): 55-62 (2014)
non-patent document 4: PLOS ONE, 9(6): e98319 (2014)
non-patent document 5: Cytotherapy, 15:578-585 (2013)
non-patent document 6: PLOS ONE, 9(8): e106110 (2014)
non-patent document 7: PLOS ONE, 9(1): e85336 (2014)

SUMMARY OF THE INVENTION

Problems to be Solved by the Invention

Therefore, the present invention aims to provide a novel screening system capable of evaluating tumorigenicity conveniently in a short period.

Means of Solving the Problems

The present inventors have conducted intensive studies in an attempt to achieve the above-mentioned objective. As a result, they took note of good visibility of the anterior chamber of an eye, transplanted iPS cells as test cells into the anterior chamber of an eye of a rat, and observed the progress. As a result, they successfully detected tumorigenicity (teratoma formation) with almost 100% accuracy only in 4 weeks, which resulted in the completion of the present invention.

Accordingly, the present invention is as follows.
[1] A method for evaluating tumorigenicity of a test cell, comprising transplanting the cell into anterior chamber of an eye of an experimental animal, and observing the presence or absence of tumor formation.
[2] The method of [1], wherein the observation period is 4-8 weeks.
[3] The method of [1] or [2], wherein the number of the cells to be transplanted is not less than $10^5$ cells.
[4] The method of [3], wherein the number of the cells to be transplanted is $10^5$ cells-$10^7$ cells.
[5] The method of any of [1] to [4], wherein the experimental animal is an immunodeficient animal.
[6] The method of any of [1] to [5], wherein the experimental animal is a rat.
[7] The method of any of [1] to [6], wherein the test cell is a stem cell or a differentiated somatic cell induced therefrom.
[8] The method of any of [1] to [6], wherein the test cell is a cancer cell.
[9] The method of [8], comprising further administering a test compound to an experimental animal, and evaluating an antitumor activity of the compound by using tumor formation as an index.

Effect of the Invention

According to the present invention, tumorigenicity evaluation, which previously required several months of observation period and a large number of animals, can be shortened to about 4 to 8 weeks and the number of animals can be decreased.

DESCRIPTION OF EMBODIMENTS

Figure 1:
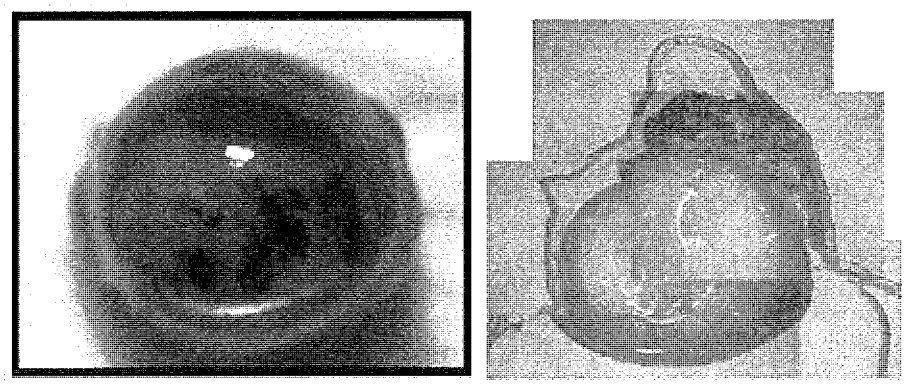
FIG. 1 shows the protocol of a tumorigenicity test using the anterior chamber of an eye.
Figure 1:
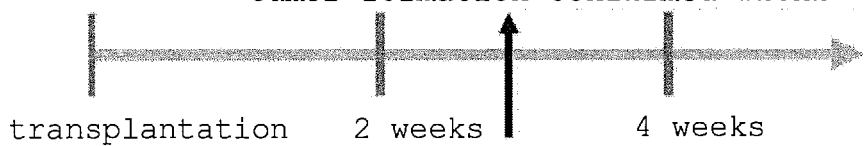
Figure 1:
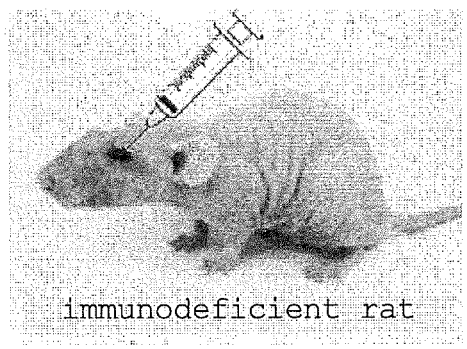

The present invention is explained in more detail in the following. Unless particularly indicated, the terms used in the present specification have the meanings generally used in the pertinent field.

The present invention is a method for evaluating tumorigenicity of a test cell, comprising transplanting the cell into anterior chamber of an eye of an experimental animal, and observing the presence or absence of tumor formation (hereinafter to be also referred to as "the evaluation method of the present invention"). As used herein, the "tumorigenicity" is used to encompass the ability to form teratomas of not only cancer cells but also undifferentiated cells.

The experimental animal to be used in the present invention is not particularly limited as long as it is an experimental animal having an anterior chamber of an eye having a sufficient volume for receiving injection of about $1 \times 10^6$ cells. For example, rat, rabbit, guinea pig, dog, cat and the like can be mentioned. Preferred are rat, rabbit, guinea pig, and more preferred is rat.

The non-human animal to be used in the present invention is desirably genetically and microbiologically controlled such that it is suitable for undergoing the obtained evaluation experiment of the present invention using the animal model. That is, genetically, use of an inbred strain is preferable. For example, in the case of rat, Wistar strain, Sprague-Dawley strain and the like can be exemplified. Microbiologically, SPF or one of a gnotobiotic grade is preferably used.

Sex, age and the like of the experimental animal is not particularly limited as long as the volume of the anterior chamber of an eye can meet the above-mentioned conditions. One with any sex, age can be used according to the animal species.

The test cell to be the evaluation target of the evaluation method of the present invention is preferably a human cell in consideration of applicability to regenerative medicine and use as a screening system for anticancer drugs. Thus, in one embodiment, the experimental animal to be used for the evaluation method of the present invention is desirably an immunodeficient animal so that human cells are not rejected. For example, in the case of rat, for example, F344/NJcl-rnu/rnu rat lacking T cell function, SCID rat, X-SCID rat, FSG rat lacking both genes of SCID and XSCID and the like can be mentioned.

However, eye is an immune-privileged site and is known to be less likely to reject transplanted cells. Thus, in another embodiment, a normal animal having a normal immune system can also be used as an experimental animal. Since immunodeficient animals are limited in species and expensive, the use of normal experimental animals is extremely significant in increasing the broad utility of the evaluation method of the present invention.

The test cell to be the evaluation target of the evaluation method of the present invention is not particularly limited as long as it may have tumorigenicity and any cell can be used. In preferable one embodiment, since the evaluation method of the present invention is used for evaluating safety of cells for transplantation, the test cell is exemplified by pluripotent stem cells such as embryonic stem cell (ES cell), induced pluripotent stem cell (iPS cell), mesenchymal stem cell (MSC) and the like, somatic stem cell (e.g., neural stem cell etc.), somatic cell (e.g., corneal cell, hepatocyte, kidney cell, pancreatic β cell, cardiac muscle cell, blood cells etc.) obtained therefrom by differentiation induction, and tissues (e.g., cornea, retinal pigment epithelium, hepatic tissue, kidney tissue, pancreatic tissue, cardiac muscle etc.) formed therefrom. In consideration of the fact that the in vivo test is necessary for evaluating tumorigenicity under influence of the microenvironment of the transplantation site, preferably, the test cell is desirably a cell or tissue constituting the eye. Even cells constituting other tissues can be applied to the evaluation method of the present invention as a primary screening means prior to a test at the transplantation site.

In another embodiment, the evaluation method of the present invention is used for evaluation of cancer malignancy or as a screening system for anticancer drugs. Thus, various cancer cells (e.g., cancer cell collected from patients by biopsy and the like, cancer cell line etc.) can also be used as the test cells.

The test cell may be derived from any animal. Preferred are cells derived from warm-blooded animal such as human and pet animal (e.g., dog, cat etc.) or domestic animal (e.g., bovine, swine etc.) or poultry (e.g., chicken, duck etc.) and the like. More preferred is a human cell.

The number of test cells necessary for the evaluation method of the present invention is not particularly limited as long as it is not less than $10^5$ cells. In consideration of the volume of the anterior chamber of an eye which is the transplantation site, it is preferably $10^5$ cells-$10^7$ cells. International guidelines proposed by WHO indicate transplantation of $10^7$ cells. Using the evaluation method of the present invention, however, tumorigenicity can be detected with about 60% accuracy by using $10^5$ cells, and nearly 100% accuracy by using $10^6$ cells. More preferably, therefore, the number of the test cells is $10^5$ cells-$10^6$ cells, particularly preferably about $10^6$ cells (e.g., not less than $5 \times 10^5$ cells and less than $5 \times 10^6$ cells).

The test cells can be used for transplantation by suspending the above-mentioned amount in, for example, 5-10 μl of a suitable medium or isotonic solution (e.g., saline, PBS etc.). To increase the retentivity of the test cells in the anterior chamber of an eye, the cell suspension can be transplanted into the anterior chamber of an eye after mixing with an extracellular matrix known per se such as Matrigel and the like.

The anterior chamber of an eye is a region inside the eye between the iris and the endothelial cells in the innermost layer of the cornea and is filled with aqueous humor. The anterior chamber of an eye allows easy monitoring of the state of the transplanted cells at any time through the cornea, and can detect tumor formation conveniently and early. The test cells can be transplanted into the anterior chamber of an eye by injecting the cell suspension prepared above from the corneal limbic area of the eye. Transplantation may be performed for one eye, and the other eye can be used as a control.

After transplantation, experimental animals can be bred in the same way as before transplantation. The follow-up can be performed, for example, by visually observing tumor formation under a stereomicroscope at appropriate intervals. In the evaluation method of the present invention, for example, when the tumor formed occupies ¼ or more of the inner volume of the anterior chamber of an eye, (tumorigenic) death can be determined.

In addition, after a certain period of time, the eyeballs may be removed and formation of tumor including teratomas can be confirmed by tissue staining (e.g., HE staining, immunostaining by tissue specific marker) and the like.

In conventional evaluation by subcutaneous transplantation, a tumor cannot be determined until it grows to a size of about 20 mm, and during that time, observation is not possible since it is under the skin. In contrast, in the evaluation method of the present invention, tumor formation can be detected sharply since transplanted cells can be observed at any time while the experimental animals are alive. Therefore, nearly 100% of tumor formation can be detected at 4 weeks post-transplantation, depending on the kind of test cells and the number of transplanted cells. Even when the number of cells to be transplanted is as small as about $10^5$ cells, tumor formation can be detected with high accuracy within 8 weeks after transplantation.

Therefore, the period of follow-up in the evaluation method of the present invention is preferably 4-8 weeks.

In the evaluation method of the present invention, the presence or absence of tumorigenicity can be evaluated with sufficient accuracy when the number of experimental animals is 5. International guidelines proposed by WHO indicate testing using 10 individuals. Since the evaluation method of the present invention has less variation between individuals, it is also advantageous in that the number of individuals used for evaluation can be reduced from those used conventionally.

In the evaluation method of the present invention, by using a cancer cell, for example, a cancer cell collected from a patient as a test cell, malignancy of the cancer cell can be evaluated. For example, first, the evaluation method of the present invention is performed on cancer cells known to have low clinical malignancy, the number of transplanted cells in which cancer cells do not proliferate is determined, after which the test cancer cells in the above number are transplanted into the anterior chamber of an eye of the experimental animal and follow-up is performed. When tumor formation is found, the test cancer cell can be judged to have high malignancy.

In the evaluation method of the present invention, a cancer cell, for example, various cancer cell lines conventionally used for the evaluation of anticancer drugs, is used as a test cell, a candidate compound for an anticancer drug is administered as a test compound to an experimental animal, tumor formation in the anterior chamber of an eye of the experimental animal is examined, whereby a test compound having an antitumor activity can be screened for. For example, the number of transplanted cells in which a test cancer cell line can form a tumor is first determined, after which the test cancer cells in the above number are transplanted and the test compound is administered into the anterior chamber of an eye of the experimental animal and follow-up is performed. When suppression of tumor formation is observed, the test compound can be judged to have an antitumor activity. The test compound can be administered to the experimental animal by any administration route and dose. In preferable one embodiment, it can be administered topically to the eye. Topical administration to the eye may be performed by injection into the anterior chamber of the eye as in the cell transplantation, or may be performed by instillation. In this case, cancer cells may be transplanted into both eyes, the drug may be administered to only one eye, and the suppressive effect on tumor formation can also be evaluated by comparing the both eyes.

By practicing the evaluation method of the present invention for a compound selected as having an antitumor activity as a result of primary screening using a cancer cell line, or an existing anticancer drug, and by changing the test cells to a cancer cell derived from a patient, an anticancer drug effective for the patient can be selected, and a personalized cancer treatment can be performed.

While the present invention is more specifically explained by referring to the following Examples, it is needless to say that the present invention is not limited thereto.

EXAMPLE (1) Method

As an experimental animal, an immunodeficient rat F344/NJcl-rnu/rnu (5-week-old, CLEA Japan, Inc.) was used. A mixed anesthesia solution of three types of Domitor (medetomidine hydrochloride) (75 µg/ml), Dormicum (Midazolam) (0.4 mg/ml), Betorphal (butorphanol tartrate) (0.5 mg/ml) was intraperitoneally injected at 500 µl/100 g to perform systemic anesthesia. In addition, topical anesthesia was performed with Benoxil (0.4%, Oxybuprocaine Hydrochloride eye drop) instillation. A mixed solution of a cell suspension containing 5 µl human iPS cell line 201B7 (cell.brc.riken.jp/ja/hps/hps0063_info) or FFI-01 (cira.kyoto-u.ac.jp/ciRA Center for iPS Research, Kyoto University) ($1\times10^4$ cells-$1\times10^7$ cells), and a solution containing Matrigel (5 µl) was injected into one eye of rats (5 rats in each group) placed under a stereomicroscope. As an antibacterial agent, a cravit instillation solution (0.5%, levofloxacin hydrate) was instilled. After transplantation, rats were followed-up for a certain period (immediately thereafter to several months). Thereafter, for more detailed analysis, the rats were euthanized by intraperitoneal overdose of pentobarbital (120 mg/kg). The eyeballs were collected, HE staining etc. was performed, and teratoma formation (differentiation into lineages of three germ layers) was confirmed. The protocol of this test is shown in FIG. 1.

2) Results

Figure 2:
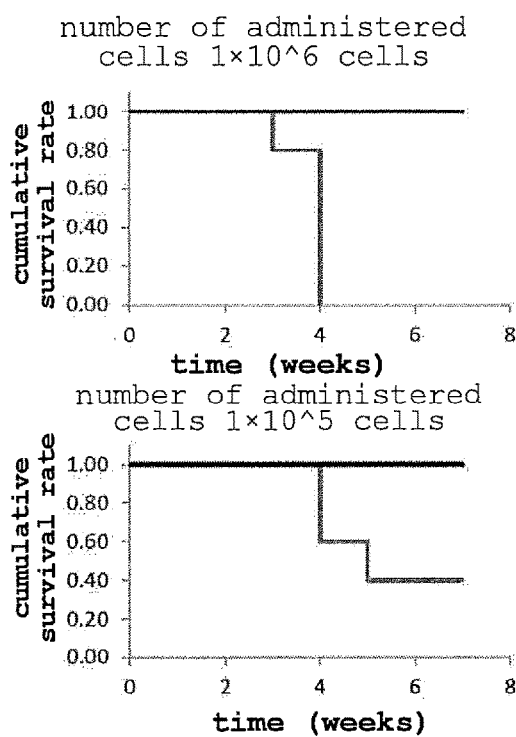
FIG. 2 shows teratoma formation (right) and cumulative survival rate (left) at one month after administration of human iPS cell 201B7 line within the anterior chamber of an eye of an immunodeficient rat.
Figure 2:
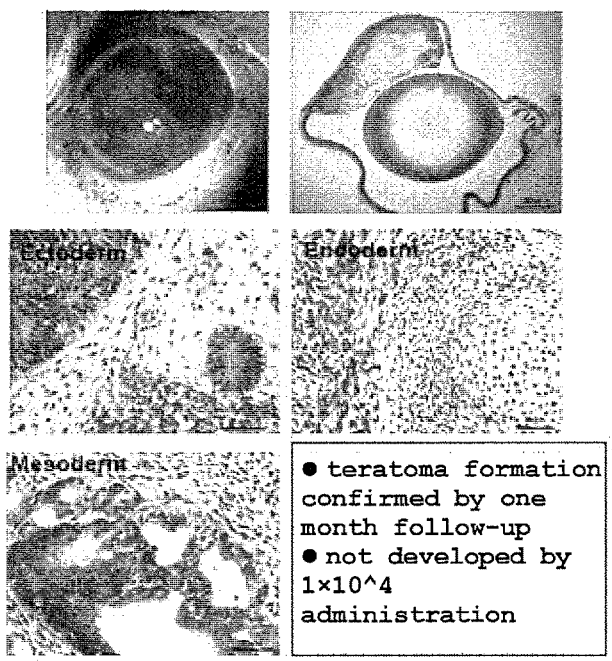
Figure 3:
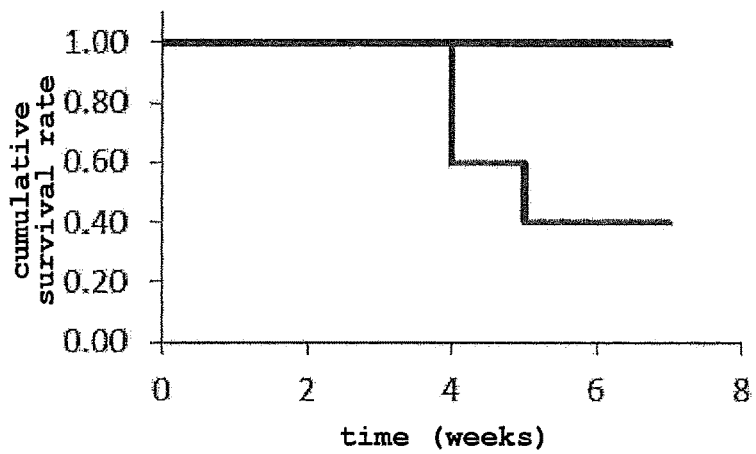
FIG. 3 shows teratoma formation (lower) and cumulative survival rate (upper) at one month after administration of human iPS cell FFI-01 line within the anterior chamber of an eye of an immunodeficient rat.
Figure 3:
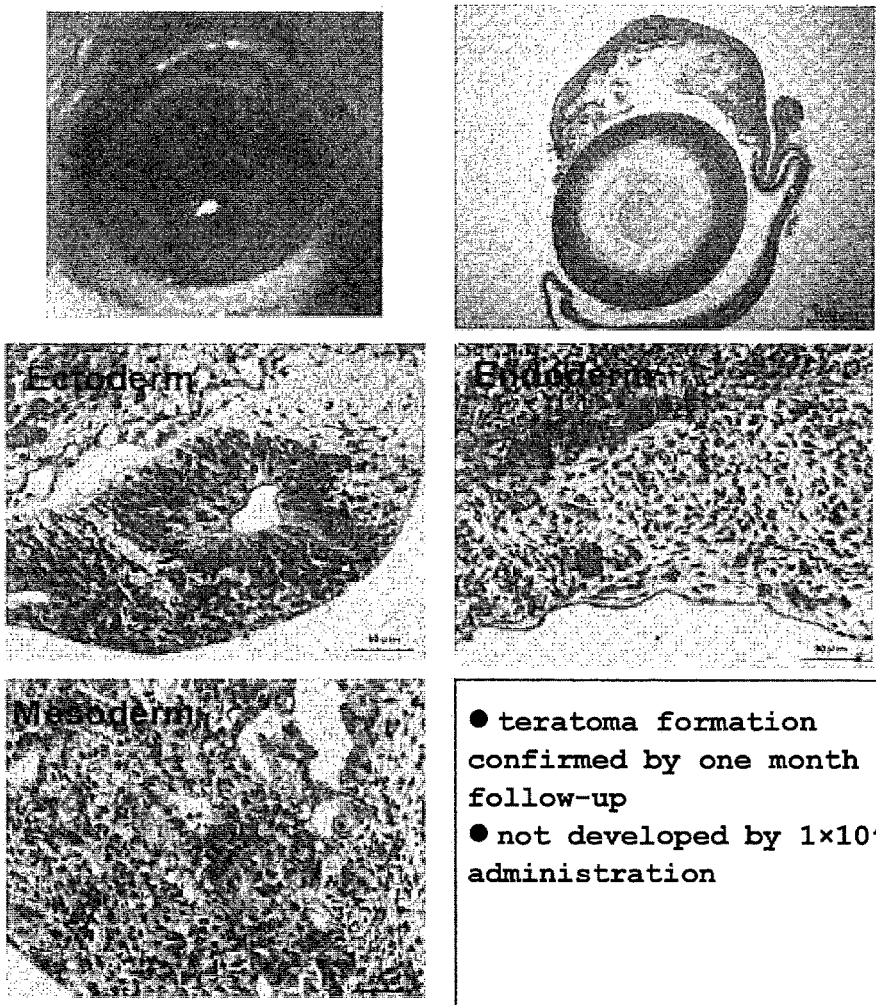

Tumor formation occupying ¼ or more of the anterior chamber inner volume was determined to mean dead, and Kaplan-Meier survival curve was generated. In the case of 201B7 line, when $1\times10^6$ cells were transplanted, all five rats were judged dead (with teratoma formation ability) at 4 weeks after transplantation (FIG. 2, upper left). As a result of HE staining, differentiation into lineages of three germ layers was confirmed (FIG. 2, right). Even when $1\times10^5$ cells were transplanted, 60% (⅗ rats) were judged dead within 8 weeks (FIG. 2, lower left). Even when FFI-01 line was transplanted, similar results were obtained (FIG. 3). When $1\times10^7$ cells were transplanted, all rats were judged dead at 4 weeks post-transplantation for any iPS cell line. On the other hand, when 1×10⁴ cells were transplanted, tumor formation was not found in any cell line.

In conventional evaluation by subcutaneous transplantation, a tumor cannot be determined until it grows to a size of about 20 mm, and during that time, observation is not possible since it is under the skin. In contrast, in the evaluation method of the present invention, tumor formation can be detected sharply since transplanted cells can be observed at any time while the rats are alive. Thus, tumor formation was detectable with 100% accuracy at 4 weeks post-transplantation.

INDUSTRIAL APPLICABILITY

According to the present invention, tumorigenicity evaluation, which previously required several months of observation period and a large number of animals, can be shortened to about 4 to 8 weeks and the number of animals can be decreased. Thus, the present invention is useful for in vivo screening for tumorigenicity of cells for transplantation. In addition, the present invention is extremely useful since it can be utilized for evaluation of cancer malignancy or as a screening system for anticancer drugs.

This application is based on a patent application No. 2017-148605 filed in Japan (filing date: Jul. 31, 2017), the contents of which are hereby incorporated by reference in full herein.

The invention claimed is:

1. A method for evaluating tumorigenicity of test cells, comprising transplanting at least $10^5$ of the test cells into the anterior chamber of an eye of an experimental, immunodeficient animal, and observing the presence or absence of tumor formation at least 4 weeks post transplantation.

2. The method according to claim 1, wherein the presence or absence of tumor formation is observed 4-8 weeks post transplantation.

3. The method according to claim 1, wherein $10^5$ cells-$10^7$ test cells are transplanted.

4. The method according to claim 1, wherein the experimental, immunodeficient animal is a rat.

5. The method according to claim 1, wherein the test cells are stem cells or differentiated somatic cells induced therefrom.

6. The method according to claim 1, wherein the test cells are cancer cells.

7. The method according to claim 6, comprising further administering a test compound to the experimental, immunodeficient animal, and evaluating an antitumor activity of the compound by using tumor formation as an index.

8. The method according to claim 2, wherein $10^5$ cells-$10^7$ test cells are transplanted.

9. The method according to claim 2, wherein the experimental, immunodeficient animal is a rat.

10. The method according to claim 9, wherein the test cells are stem cells or differentiated somatic cells induced therefrom.

11. The method according to claim 10, wherein the test cells are cancer cells.

12. The method according to claim 11, comprising further administering a test compound to the experimental, immunodeficient animal, and evaluating an antitumor activity of the compound by using tumor formation as an index.

* * * * *